US008787523B2

(12) United States Patent
Sackett

(10) Patent No.: US 8,787,523 B2
(45) Date of Patent: Jul. 22, 2014

(54) X-RAY ANALYSIS APPARATUS WITH RADIATION MONITORING FEATURE

(75) Inventor: Don Sackett, Bedford, MA (US)

(73) Assignee: Olympus NDT, Inc., Waltham, MA (US)

( * ) Notice: Subject to any disclaimer, the term of this patent is extended or adjusted under 35 U.S.C. 154(b) by 346 days.

(21) Appl. No.: 13/135,345

(22) Filed: Jul. 1, 2011

(65) Prior Publication Data

US 2013/0003923 A1    Jan. 3, 2013

(51) Int. Cl.
*G01N 23/223* (2006.01)

(52) U.S. Cl.
USPC .............................................. 378/44; 378/117

(58) Field of Classification Search
USPC ................ 378/44, 108, 102, 45, 42, 145, 117
See application file for complete search history.

(56) References Cited

U.S. PATENT DOCUMENTS

| 3,984,733 | A | * | 10/1976 | De Lucia | 361/2 |
| 4,158,138 | A | * | 6/1979 | Hellstrom | 378/116 |
| 6,965,118 | B2 | | 11/2005 | Martin et al. | |
| 7,375,358 | B1 | | 5/2008 | Martin et al. | |
| 7,375,359 | B1 | | 5/2008 | Grodzins | |
| 7,430,274 | B2 | | 9/2008 | Connors et al. | |
| 7,639,784 | B2 | * | 12/2009 | Feda | 378/118 |
| 7,671,350 | B2 | | 3/2010 | Grodzins | |
| 2008/0152079 | A1 | | 6/2008 | Tannian et al. | |
| 2009/0232282 | A1 | * | 9/2009 | Belson et al. | 378/203 |
| 2010/0097229 | A1 | * | 4/2010 | Hornig et al. | 340/600 |
| 2010/0133450 | A1 | * | 6/2010 | Belson | 250/519.1 |
| 2011/0150185 | A1 | * | 6/2011 | Uzbelger Feldman | 378/191 |

FOREIGN PATENT DOCUMENTS

WO    WO 00/37928    6/2000

OTHER PUBLICATIONS

Ryong-Joon Roe. Method of X-ray and Neutron Scattering in Polymer Science. Oxford University Press, 2000. 1st edition.*

* cited by examiner

*Primary Examiner* — Hoon Song
(74) *Attorney, Agent, or Firm* — Iandiorio Teska & Coleman, LLP

(57) ABSTRACT

An XRF analysis apparatus includes a housing with a source of penetrating radiation to be directed at a sample and a detector for detecting fluoresced radiation from the sample. A shield is attachable to the housing to protect the user from radiation and a safety interlock is configured to detect whether or not the shield is attached to the housing. A controller is responsive to the safety interlock, and configured to monitor usage of the source of radiation at or above a predetermined power level when the shield is not attached to the housing and provide an output signal when the monitored usage of the source of penetrating radiation at or above the predetermined power level without the shield attached to the housing exceeds one or more predetermined thresholds.

14 Claims, 5 Drawing Sheets

X-RAY ANALYSIS APPARATUS WITH RADIATION MONITORING FEATURE

FIELD OF THE INVENTION

The invention relates to x-ray devices.

BACKGROUND OF THE INVENTION

X-ray devices such as handheld x-ray fluorescence (XRF) instruments are known as are various shields for such instruments. See U.S. Pat. Nos. 7,430,274; 7,375,359; 7,375,358; 6,965,118; and 7,671,350 as well as WO 00/37928 all incorporated herein by this reference. See also U.S. Published Application No. US-2008-0152079.

The shields for these devices, typically attached to the nose of the instrument, serve to protect the user of the device from radiation. Radiation limits are usually established by regulations which may vary by jurisdiction.

For handheld XRF devices with lower power x-ray tubes (e.g., below about 4 watts and producing about 40 keV), reaching a radiation limit is not as big a concern as with higher power x-ray tubes (e.g., those producing 50 keV and above) used in some industries. This is because at tube voltages of 50 keV and higher, a greater amount of x-ray radiation between 40 keV and 50 keV is produced. These energies are harder to shield while still maintaining the small size and minimal weight needed for a handheld device. Thus there are more x-rays emitted from the device, than in lower voltage portable XRF devices. In addition, the 40 keV-50 keV x-rays are more likely to scatter multiple times within a sample, rather than be absorbed by the sample, and then be directed back towards the operator. Also, in some instruments, the power output by the x-ray tube can be varied (e.g., between 40 keV and 50 keV).

BRIEF SUMMARY OF THE INVENTION

Some portable XRF devices have been introduced with an external shield over the end of the unit, where the x-rays are emitted. While this shielding does reduce radiation levels external to the device, compared to with the external shield removed, using an external shield has a number of disadvantages. Shielding can be misplaced or may be removed from the instrument by the user. Some shield designs can also be bulky and interfere with normal usage of the instrument especially when testing smaller samples. It may be hard to position the portable XRF device so that the desired area of a sample is being irradiated. Shields also generally add weight to the XRF instrument, and negatively impact the ergonomics, making them "end heavy" and unbalanced since the externally added shields are often at the end of the pistol-shaped XRF device.

If a user operates a higher power XRF instrument without the shield installed, the user often does not know if he has been exposed to the maximum allowed amount of radiation nor does he know his current usage time or how his current usage time relates to the maximum amount of radiation allowed. Typically, the maximum allowed amount of radiation is indicated in regulations maintained by an allowed body in the region where the XRF instrument is used.

Featured is an XRF analysis apparatus comprising a housing with a source of penetrating radiation to be directed at a sample and a detector for detecting fluoresced radiation from the sample. A shield is attachable to the housing to protect the user from radiation. A safety interlock is configured to detect when the shield is attached to the housing. A controller is responsive to the safety interlock and configured to monitor usage of the source of radiation at or above a predetermined power level (e.g., 50 keV) when the shield is not attached to the housing and to also provide an output signal when the monitored usage of the source of penetrating radiation at or above the predetermined power level without the shield attached to the housing exceeds one or more predetermined thresholds.

In one example, a predetermined threshold is a first percentage (e.g., less than 5%) of a maximum allowable allowed dose. When the monitored usage of the source exceeds this first percentage of the maximum allowable allowed dose, the output signal provided includes a first notification or message to the user noting the monitored usage and the percentage of the maximum allowable allowed dosage. Another predetermined threshold can be a second percentage (e.g., less than 15%) of the maximum allowable allowed dose. When the monitored usage of the source exceeds that percentage, the output signal provided is designed to provide a second notification to the user. Still another predetermined threshold can be a third percentage (e.g., 50% or less) of a maximum allowable allowed dose and when the monitored usage of the source exceeds that percentage of the maximum allowable allowed dose, the output signal provided is configured to prevent the operation of the source at or above the predetermined power level until the shielding is attached to the housing. Another predetermined threshold might be a fourth percentage (e.g., around 100%) of the maximum allowable allowed dose and when the maximum usage of the source equals or exceeds that percentage of the maximum allowable allowed dose, the output signal can be configured to prevent the operation of the source at any power level even if the shield is attached.

The safety interlock may include a circuit associated with the shield providing a signal to the controller when the shield is attached to the housing. In one version, there are contacts on the shield in communication with the circuit and the housing includes contacts for communicating the signal.

An x-ray analysis method in accordance with the invention includes detecting when an x-ray device includes a shield attached thereto, determining if the x-ray device is being operated at or above a predetermined power level without the shield attached, monitoring usage of the device at or above the predetermined power level when the shielding is not attached, and taking one or more actions when the monitored usage of the device without the shield attached exceeds one or more predetermined thresholds.

One preferred version of the invention, in some aspects, relates to a safety interlock configured to detect when the shield is attached to a handheld XRF instrument and, when it is not, the usage time is monitored and action is taken when the usage time meets or exceeds a predetermined percentage of the maximum allowed radiation exposure. The level of the allowed exposure, and warnings when an operator may have reached certain levels of exposure limits (i.e., 5%, 10%, 50%) can be set at the factory of by a supervisor based on specific allowed limits or company policies. Access to change this setting is preferably password protected.

The subject invention, however, in other embodiments, need not achieve all these objectives and the claims hereof should not be limited to structures or methods capable of achieving these objectives.

BRIEF DESCRIPTION OF THE SEVERAL VIEWS OF THE DRAWINGS

Other objects, features and advantages will occur to those skilled in the art from the following description of a preferred embodiment and the accompanying drawings, in which.

DETAILED DESCRIPTION OF THE INVENTION

Figure 1:
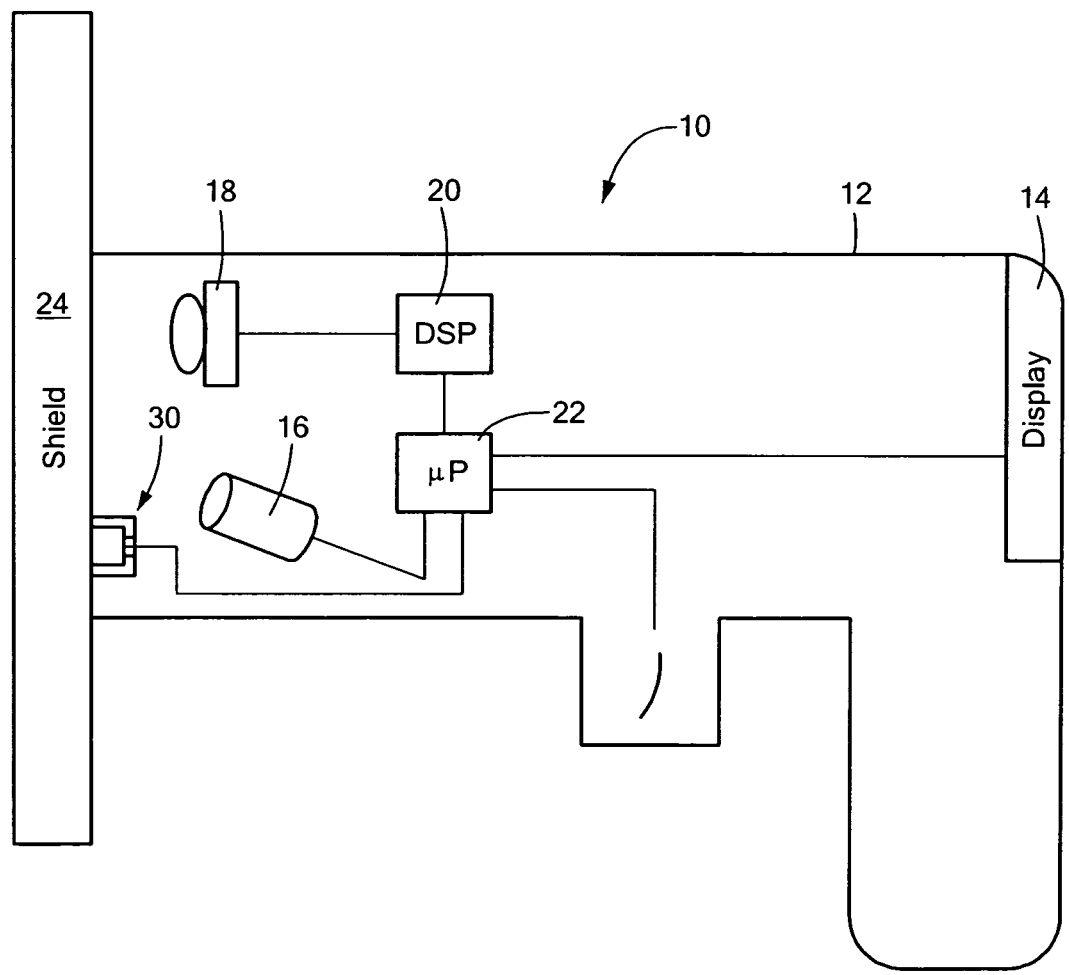
FIG. 1 is a schematic diagram showing the primary components associated with an XRF instrument in accordance with an example of the invention.

Aside from the preferred embodiment or embodiments disclosed below, this invention is capable of other embodiments and of being practiced or being carried out in various ways. Thus, it is to be understood that the invention is not limited in its application to the details of construction and the arrangements of components set forth in the following description or illustrated in the drawings. If only one embodiment is described herein, the claims hereof are not to be limited to that embodiment. Moreover, the claims hereof are not to be read restrictively unless there is clear and convincing evidence manifesting a certain exclusion, restriction, or disclaimer.

FIG. 1 shows an example of an x-ray analysis apparatus, in this particular example, a handheld "open beam" XRF instrument 10 including gun shaped housing 12 with display 14 and containing, inter alia, x-ray source 16 and detector 18 with digital signal processing subsystem 20 which analyzes radiation detected by detector 18. An open beam system is one where the primary beam exists the device and strikes a sample, and the sample is not within an enclosure for shielding. Source 16 generates x-rays (e.g., between 8 to 50 keV) delivered to a sample and detector 18 detects fluoresced radiation from the sample in order to analyze the elemental make up of the sample. Processing means such as processor or microcontroller 22 or another computerized device, among other things, controls the operation of source 16 and presents data as analyzed by DSP 20 to display 14. It should be noted that display 14 may instead be a different type of indication apparatus to convey the data, such as a speaker with an audio message or indicating lights. One suitable example of an XRF instrument is the "Delta" line of XRF analyzer products available from Olympus Innov-X (Woburn, Mass.).

As noted above, shield 24 is attached to housing 10 in order to protect the user from radiation. The term "shield" as used in the present disclosure is intended to denote a device that prevents the user of the XRF instrument from being exposed to a "maximum allowed dose" of radiation. Examples of shields may take the form of an x-ray absorbing material, such as lead, or a displacement apparatus that maintains a minimum distance between the user and the x-ray source. The invention features, in one aspect, safety interlock 30 configured to detect when shield 24 is attached to housing 12. Controller 22 is responsive to safety interlock 30 and is configured to monitor usage of source 16 at or above a predetermined power level (e.g., 40 or 50 keV) when shield 24 is not attached as detected by safety interlock 30. Controller 22 is further configured to provide one or more output signals when the monitored usage without the shield attached at the predetermined power level exceeds one or more predetermined thresholds. The signal output can vary in functionality from providing a simple message or warning to interrupting further usage of the instrument at one or more or perhaps even all power levels. The predetermined power level which triggers the monitoring function can be set at the factory, by a supervisor, or by the user. The predetermined thresholds can be tied to allowed radiation limits and can also be set at the factory, by a supervisor, or by the user, in each case preferably requiring a password to prevent unauthorized access.

In but one example, table 1, below, delineates the signal output by controller 22 for 50 keV operation:

TABLE 1

| Monitored Condition | Signal |
| --- | --- |
| Usage time greater than or equal to 0.02 of the maximum allowed dose signal | Message: Recommend usage of shielding and report usage time and percentage of maximum allowed dose. |
| Usage time greater than or equal to 0.1 of the maximum allowed dose. | Message: Recommend usage of shield and provide a warning indicating user has reached 10% of the maximum allowed dose. |
| Usage time is greater than or equal to 0.2 of the maximum allowed dose. | Prohibit usage at 50 keV and notify user. |
| Usage time is greater than or equal to maximum allowed dose. | Prohibit usage at all power levels. |

The radiation levels are not typically directly monitored by the device but based on known radiation levels as a function of source power levels, as measured at various distances and locations around the device. So for example, it is conservative to assume a maximum operator usage time of 8 hours/day, 5 days/week, 50 weeks per year thus a total usage time of 2,000 hours/year. The software and processor log the total time of use of the device without the shield present, and multiply by the known radiation levels (typically in units of mrem/hr or uSv/hr), to determine the maximum exposure at any particular time. Warnings based on maximum exposure levels using Table 1 can then be presented to the operator.

The fact that this is a processor-based system offers additional advantages and flexibility. The radiation exposure levels are easily scaled from the measured values, for other tube power levels. The processor 22 and software can perform this function to obtain a better estimate of the exposure at any time rather than using the measured values based on maximum source power. In addition, multiple operators, with different logins and passwords, may be tracked, since many portable XRF devices are shared.

Figure 2:
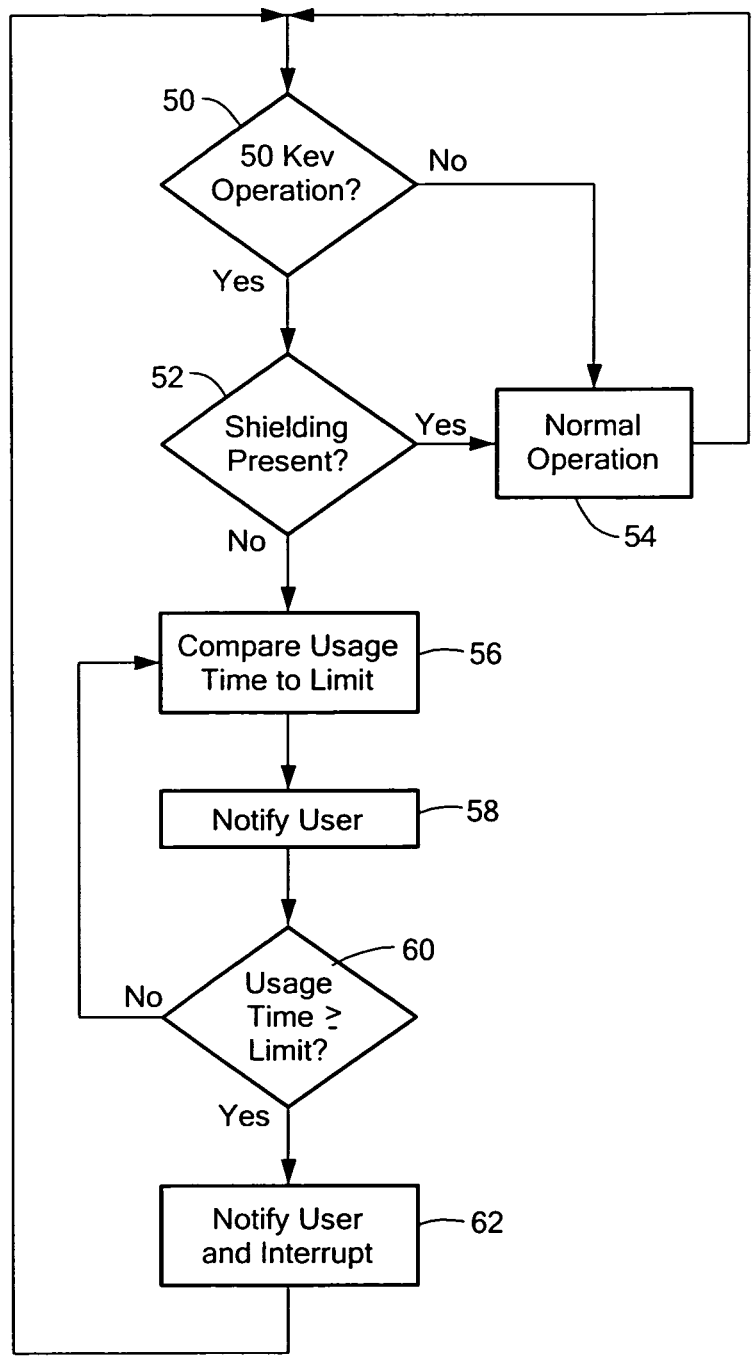
FIG. 2 is a flow chart depicting the primary steps associated with the processing of the controller shown in FIG. 1.

Thus, processor 22 is programmed, in this example, to detect whether the instrument is being operated at 50 keV, step 50, FIG. 2 and if so to detect whether or not the shielding is present, step 52. If the shielding is present and/or operation is below 50 keV, normal operation ensues, step 54. If the device is being operated at 50 keV and shielding is not present, the usage time is monitored and compared to one or more limits, step 56. At different thresholds, the usage time can be provided to the user as a notification, step 58. If the usage time is greater than or equal to some limit, step 60, then the user is again notified, step 62 and/or an interrupt function is generated prohibiting, as noted above, operation at 50 keV.

In one specific example, the predetermined thresholds of Table 1 can vary and can be set at the factory, by a supervisor, or by the user. The same is true with respect to percentages noted in Table 1 (e.g., 2%, 10%, 20% and the like). A first notification percentage of less than 5% and a second notification percentage of less than 15% are recommended. Discontinued operation at 50 keV without the shield can be set at a percentage of less than 50% and discontinued operation at any power level can be set at or near 100% of the maximum allowed usage.

Figure 3:
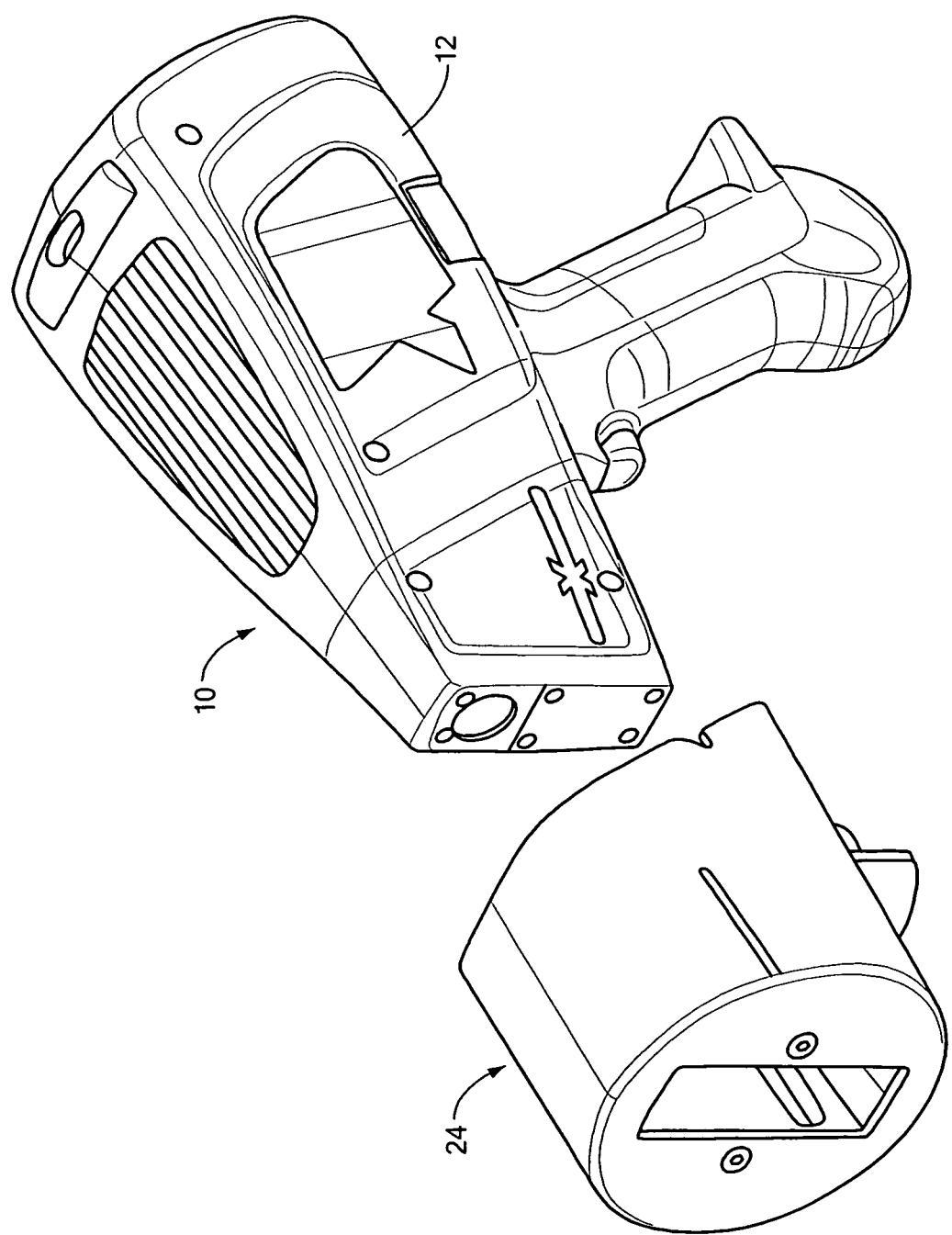
FIG. 3 is a schematic front view showing an XRF instrument and its corresponding shield about to be coupled thereto.
Figure 4:
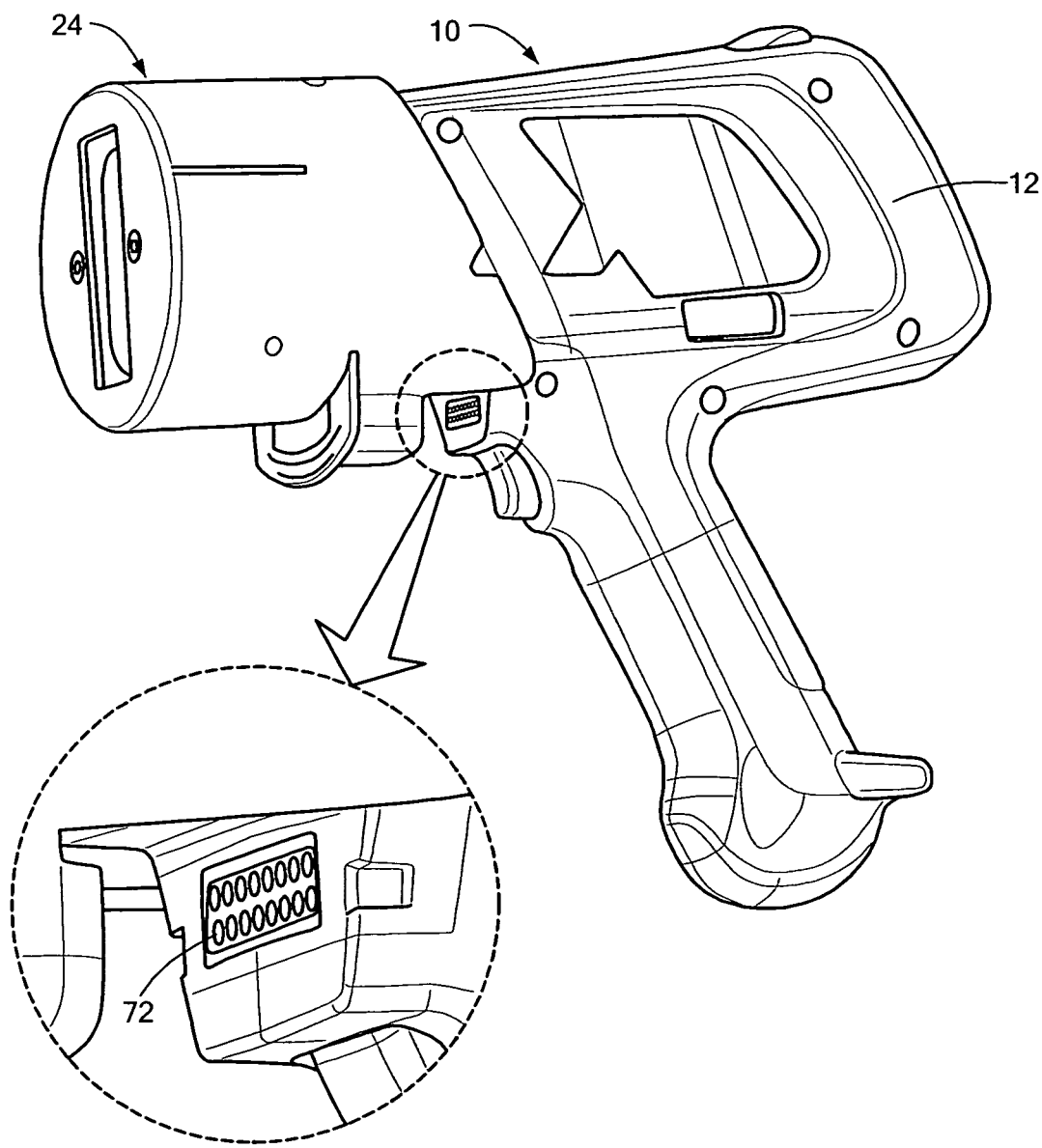
FIG. 4 is a schematic side view showing the shield now attached to the XRF instrument.
Figure 5:
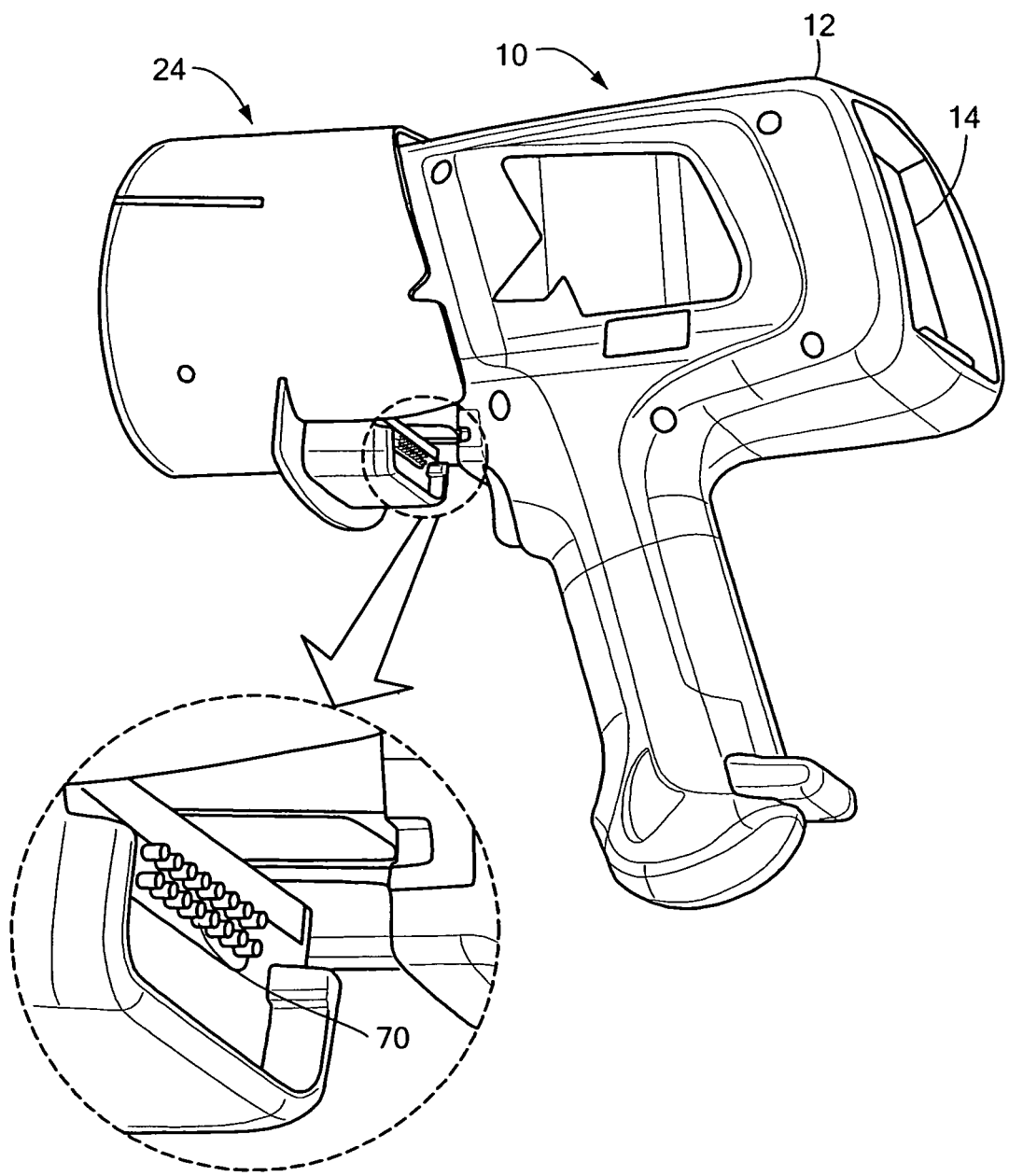
FIG. 5 is another schematic side view showing how the shield is mechanically and electrically coupled to the XRF instrument.

Figs. 3-5 depict an example where shield 24 includes a circuit (connected to male pins 70, FIG. 5) providing a signal to controller 22, FIG. 1 when the male pins are received in female sockets 72, FIG. 4 of housing 10. When the shield is not present, the signal is not provided to controller 22, FIG. 1. The presence of an additional I2C module and a key found in an identification register functions to alert the controller software that additional shielding is present and it is safe to enable a 50 keV mode. Pins (such as pogo pins) 70, FIG. 5 establish an electrical connection with the instrument's main external interface as shown at 72 in FIG. 4. Other conductive contacts may be used. An I2C silicon serial number chip signals that a guard is in place. It should be noted that a variety of techniques may be used to detect the presence of shield 24, such as an embedded hall effect, or optical sensor. Furthermore, the electrical interface for the presence detection system is not intended to be limited to the exemplary I2C module. The shield or guard could also be present in a test stand or work station and thus the shield shown in the figures is not a necessary limitation of the invention. In such cases, the invention determines whether the instrument is present in the test stand or work station (which include shielding).

A functional specification for the software operating on controller 22, FIG. 1 in one preferred embodiment, is as follows. At the factory, user interface allows a technician to modify shielding options such as a) always requiring operation of the instrument in connection with the workstation, b) always requiring the presence of a shield or a workstation, or c) monitoring usage and providing warnings (as discussed above). The default setting is typically always requiring a shield. A user menu allows an option entitled "allowed levels" with two settable parameters: the maximum allowed dose and the units (either mSv or mR). If the user changes units, a warning dialog box pops up reading "please verify that the maximum dosage entered is correct for the selected units (1 mSv=100 mR)". The software calculates and stores the time required to reach the predetermined cumulative exposure time limit in seconds, which in this exemplary case is annual. Assuming a maximum dosage of 15 mR/hr or 0.15 mSv/hr then:

Time limit (sec)=max allowed dose×240 (for a maximum allowed dose in mR)   (1)

or

Time limit (sec)=max allowed dose×24000 (for maximum allowed dose in mSv)   (2)

The software logs in seconds the amount of time the analyzer has operated at 50 keV without shielding and sums the usage time over the course of the day. Preferred software typically retains the individual data daily usage sums for a minimum of one year and stores a running yearly usage time which the sum of any daily usage amounts for the last 365 calendar days (usage time). It may be preferable to use the real elapsed time for each reading, however, it is much simpler to store the maximum test (usage) time before the test starts and assume that all tests run to the maximum time. If the always require a workstation or always require a probe shield options are selected, 50 keV operation will be prohibited unless the analyzer is attached to either the hand shield or the workstation. If the monitor usage option is selected, the software will check the usage time compared to the time limit and provide operation according to the monitoring and notification procedures described below.

At the start of any 50 keV test, the software compares the usage time to the time limit. If the usage time is greater or equal to 0.02 of the time limit, the following is displayed after each calibration check: "according to your XRF usage in the 50 keV beam setting, you have potentially produced a maximum radiation exposure at your hand equivalent to 2% of your allowed annual dose. We recommend using the probe shield for continued operation". The user must dismiss this message before continuing testing.

If the usage time is greater than or equal to 0.1 of the time limit, the following is displayed after the calibration check: "according to your XRF usage in the 50 keV beam setting, you may have potentially produced a maximum radiation exposure at your hand equivalent to 10% of your allowed annual dose. At this point you may be required by local or national regulations to monitor and record your dose. We recommend the use of dosimetry for continued operation. We also recommend the use of a probe shield." Again, the user must dismiss this message before continuing testing.

If the usage time is greater than or equal to 0.2 of the time limit, 50 keV operation is not allowed unless the hand shield or workstation is installed. The following message is displayed every time a 50 keV test is attempted: "according to your XRF usage in the 50 keV beam setting, you may have potentially produced a maximum radiation exposure at your hand equivalent to 20% of your allowed annual dose. This unit may not be operated at 50 keV without the hand shield or within a workstation. Attach the hand shield or contact the factory for further information". The user may clear this message, however, it should appear again every time the user attempts to start a test without the hand shield. If the user then operates the device at 40 keV, the following message may be displayed: according to your XRF usage in the 50 keV beam setting, you may have potentially produced a maximum radiation exposure at your hand equivalent to 20% of your allowed annual dose. Continued operation in the 40 keV modes will require a dosimetry. The user must clear this message and then continue testing at 40 keV.

If the usage time is greater than or equal to the time limit, no test is allowed to start. Thus, irrespective of the power level chosen, the device cannot be operated. For every test attempt, the following message is displayed: "according to your XRF usage in the 50 keV beam setting, you may have potentially produced a maximum radiation exposure at your hand equivalent to your allowed annual dose and operation is not recommended outside of a workstation".

Although specific features of the invention are shown in some drawings and not in others, this is for convenience only as each feature may be combined with any or all of the other features in accordance with the invention. The words "including", "comprising", "having", and "with" as used herein are to be interpreted broadly and comprehensively and are not limited to any physical interconnection. Moreover, any embodiments disclosed in the subject application are not to be taken as the only possible embodiments.

In addition, any amendment presented during the prosecution of the patent application for this patent is not a disclaimer of any claim element presented in the application as filed: those skilled in the art cannot reasonably be expected to draft a claim that would literally encompass all possible equivalents, many equivalents will be unforeseeable at the time of the amendment and are beyond a fair interpretation of what is to be surrendered (if anything), the rationale underlying the amendment may bear no more than a tangential relation to many equivalents, and/or there are many other reasons the applicant can not be expected to describe certain insubstantial substitutes for any claim element amended.

Other embodiments will occur to those skilled in the art and are within the following claims

What is claimed is:

1. An XRF analysis apparatus comprising:
   a housing including:
      a source of penetrating radiation to be directed at a sample, and
      a detector for detecting fluoresced radiation from the sample;
   a shield attachable externally to the housing to protect the user from radiation;
   a safety interlock configured to detect when the shield is attached to the housing; and
   a controller, responsive to the safety interlock, configured to:
      monitor usage of the source of radiation at or above a predetermined power level when the shield is not externally attached to the housing, and
      provide an output signal when the monitored usage of the source of penetrating radiation at or above the predetermined power level without the shield externally attached to the housing exceeds one or more predetermined thresholds.

2. The apparatus of claim 1 in which a predetermined threshold is a first percentage of a maximum allowed dose and wherein when the monitored usage of the source exceeds said first percentage of the maximum allowed dose, the output signal provided includes a first notification to the user noting the monitored usage and the percentage of the maximum allowed dosage.

3. The apparatus of claim 2 in which the first percentage is less than 5%.

4. The apparatus of claim 2 in which a predetermined threshold is a second percentage of the maximum allowed dose and when the monitored usage of the source exceeds said second percentage of the maximum allowed dose, the output signal provided includes a second notification to the user noting the monitored usage and the percentage of the maximum allowed dose.

5. The apparatus of claim 4 in which the second percentage is less than or equal to 15%.

6. The apparatus of claim 1 in which a predetermined threshold is a third percentage of a maximum allowed dose and when the monitored usage of the source exceeds said third percentage of the maximum allowed dose, the output signal provided prevents the operation of the source at or above the predetermined power level until the shielding is attached to the housing.

7. The apparatus of claim 5 in which the third percentage is less than or equal to 50%.

8. The apparatus of claim 6 in which a predetermined threshold is a fourth percentage of the maximum allowed dose and when the maximum usage of the source exceeds said fourth percentage of the maximum allowed dose, the output signal prevents operation of the source at any power level even if the shield is attached.

9. The apparatus of claim 8 in which the fourth percentage is between 50% and 100%.

10. The apparatus of claim 1 in which the predetermined power level is 50 keV.

11. The apparatus of claim 1 in which the safety interlock includes a circuit associated with the shield providing a signal to the controller when the shield is attached to the housing.

12. The apparatus of claim 11 in which the safety interlock further includes a first set of conductive contacts on the shield in communication with the circuit and the housing further includes a second set of conductive contacts, wherein the first set of conductive contacts and the second set of the conductive contacts are coupled when the shield is externally attached to the housing for communicating the signal.

13. An XRF analysis apparatus comprising:
   a housing including:
      a source of penetrating radiation to be directed at a sample, and
      a detector for detecting fluoresced radiation from the sample;
   a shield attachable to the housing to protect the user from radiation;
   a safety interlock configured to detect when the shield is attached to the housing; and
   a controller, responsive to the safety interlock, configured to:
      monitor usage of the source of radiation at or above a predetermined power level when the shield is not attached to the housing, and
      provide an output signal when the monitored usage of the source of penetrating radiation at or above the predetermined power level without the shield attached to the housing exceeds one or more predetermined thresholds including:
         a first percentage of a maximum allowed dose and wherein when the monitored usage of the source exceeds said first percentage of the maximum allowed dose, the output signal provided includes a first notification to the user noting the monitored usage and the percentage of the maximum allowed dosage, and
         a second percentage of the maximum allowed dose and when the monitored usage of the source exceeds said second percentage of the maximum allowed dose, the output signal provided includes a second notification to the user noting the monitored usage and the percentage of the maximum allowed dose.

14. An XRF analysis apparatus comprising:
   a housing including:
      a source of penetrating radiation to be directed at a sample, and
      a detector for detecting fluoresced radiation from the sample;
   a shield attachable to the housing to protect the user from radiation;
   a safety interlock configured to detect when the shield is attached to the housing; and
   a controller, responsive to the safety interlock, configured to:
      monitor usage of the source of radiation at or above a predetermined power level when the shield is not attached to the housing, and
      provide an output signal when the monitored usage of the source of penetrating radiation at or above the predetermined power level without the shield attached to the housing exceeds one or more predetermined thresholds including:
         a percentage of a maximum allowed dose and when the monitored usage of the source exceeds said percentage of the maximum allowed dose, the output signal provided prevents the operation of the source at or above the predetermined power level until the shielding is attached to the housing.

* * * * *